United States Patent [19]

Beadle et al.

[11] Patent Number: 5,078,796
[45] Date of Patent: * Jan. 7, 1992

[54] PROCESS FOR MANUFACTURING TAGATOSE

[75] Inventors: James R. Beadle, Columbia; James P. Saunders, Rockville; Thomas J. Wajda, Jr., Columbia, all of Md.

[73] Assignee: Biospherics Incorporated, Beltsville, Md.

[*] Notice: The portion of the term of this patent subsequent to Mar. 26, 2008 has been disclaimed.

[21] Appl. No.: 667,591

[22] Filed: Mar. 25, 1991

Related U.S. Application Data

[62] Division of Ser. No. 381,892, Jul. 19, 1989, Pat. No. 5,002,612.

[51] Int. Cl.$^5$ ............... C13J 1/06; C13F 1/02; C07H 1/06; C07H 3/00
[52] U.S. Cl. .................... 127/46.1; 127/36; 127/46.2; 127/58; 536/124; 536/125; 536/127
[58] Field of Search ............... 127/36, 46.1, 46.2, 127/58; 536/124, 125, 127

[56] References Cited

U.S. PATENT DOCUMENTS

| 4,067,748 | 1/1978 | Rowe | 127/36 |
| 4,156,076 | 5/1979 | Dahlgren | 536/1 |
| 4,663,449 | 5/1987 | Barker et al. | 536/125 |
| 5,002,612 | 3/1991 | Beadle et al. | 127/46.2 |

Primary Examiner—Theodore Morris
Assistant Examiner—P. L. Hailey
Attorney, Agent, or Firm—William S. Ramsey

[57] ABSTRACT

A process is disclosed for the synthesis of D-tagatose by isomerizing a mixture containing D-galactose with a metal hydroxide in the presence of a catalyst at a relatively low temperature to form an intermediate metal hydroxide-D-tagatose complex, and then neutralizing the intermediate with acid to yield D-tagatose. The method is also suitable for the synthesis of L-tagatose from L-galactose, and for the recovery of pure tagatose from crude tagatose syrups. Whey, deproteinized whey, or lactose may be used as the raw material for the D-galactose. The lactose in such cases is hydrolyzed to D-galactose and D-glucose before the isomerization step.

3 Claims, 4 Drawing Sheets

PROCESS FOR MANUFACTURING TAGATOSE

This is a division of application Ser. No. 07/381,892, filed Jul. 19, 1989, now U.S. Pat. No. 5,002,612.

BACKGROUND OF THE INVENTION

1. Field of the Invention

This invention relates to processes for the conversion of the sugar galactose to the isomeric sugar tagatose. The invention also relates to production of tagatose from lactose, whey, or deproteinized whey as raw material and to the recovery of tagatose from mixtures of sugars.

2. Description of the Related Art

Lobry De Bruyn et al, Recueil des Travaux Chimiques des Pays-Bas (1897) 16:262-273, describes the isolation of D-tagatose in low yield from the complex mixture obtained by treating D-galactose with alkali. Reichstein et al, Helv. Chim. Acta, (1934), 17:753-761, disclose the isomerization of D-galactose to D-tagatose using pyridine. Pavlouska et al, Czechoslavakia Patent No. 142,959, Mar. 31, 1971, disclose the manufacture of D-tagatose using pyridine. These processes were limited in yield by the unfavorable equilibrium which favors galactose. Hicks U.S. Pat. No. 4,273,922, June 16, 1981, discloses the addition of boric acid to aldose sugars in the presence of tertiary or quaternary amines. Boric acid complexes the ketose as it is formed and effectively shifts the equilibrium. This procedure yields about 50% D-tagatose. Removal of the boric acid after completion of the reaction is difficult and requires an expensive specialty ion exchange resin. Szeja et al, Poland Patent No. 113,487, May 15, 1952, disclose the preparation of D-tagatose from D-galactose using 1,3-dicyclohexylcarbodiimide as an isomerization and complexation agent. Kubala et al, Czechoslovakia Patent No. 221,039, Sept. 15, 1982, discloses the preparation of D-tagatose from galactose by isomerization with a strongly basic anion exchange resin in the hydroxyl form. Barker et al, European Patent Application EP0109203, May 23, 1984, disclose the isomerization of aldoses to ketoses under acidic conditions with calcium chloride. Kubala, Czechoslovakia Patent No. 8402745-A, 1985, discloses the isomerization of L-galactose to L-tagatose with ion exchangers. All of the prior art processes appear to be unsuitable for mass production of tagatose.

SUMMARY OF THE INVENTION

The ketohexoses, D-tagatose and L-tagatose, are useful as reduced calorie food sweetening and bulking agents, as intermediate for the synthesis of other optically active compounds, and as additives in detergent, cosmetic and pharmaceutical formulations.

This invention relates to the synthesis of D-tagatose or L-tagatose. More specifically, it refers to the reaction of D- or L-galactose with a metal hydroxide, under basic conditions, and in the presence of a catalyst. Under these conditions, a solid metal hydroxide-tagatose complex intermediate is formed quickly and in high yield. The intermediate, when neutralized with an acid, yields D- or L-tagatose respectively.

The process described herein comprises a two-step method for the synthesis of D- or L-tagatose from D- or L-galactose, respectively. In the first step, isomerization, D-galactose or L-galactose is contacted in a reaction vessel with a basic metal hydroxide under strongly basic conditions, in the presence of a catalyst, and at a relatively low temperature, to form an intermediate reaction product. The intermediate product is a compound of the metal hydroxide and tagatose. Depending on the particular form of the process which is used, the intermediate may be filtered from the reaction mixture before the second step, or the reaction mixture may be used directly in the second step without filtration.

In the second step, neutralization, the intermediate metal hydroxide-tagatose complex is neutralized with an acid to yield tagatose and a salt.

The process for manufacture of tagatose from whey or deproteinized whey or lactose is also disclosed. In the first step, hydrolysis, lactose is hydrolyzed by acid or enzyme catalyzed hydrolysis yielding a mixture of D-galactose and D-glucose. The D-glucose may be separated or left in the reaction solution. The subsequent steps are as described for the manufacture of D-tagatose from D-galactose.

An object of this invention is to provide a high yield manufacturing process for tagatose. An object of this invention is to provide a manufacturing process for tagatose which uses plentiful and inexpensive raw materials. An object of this invention is to provide a manufacturing process for tagatose which does not involve expensive separation steps. An object of this invention is to provide a low temperature manufacturing process for tagatose. An object of this invention is to provide a process suitable for the large scale manufacture of tagatose. Another object of this invention is to provide a manufacturing process for tagatose which is economical in operation and without adverse environmental effects. An object of this invention is to provide a process for manufacture of tagatose from whey, deproteinized whey, or lactose. A final object of this invention is to provide a process for the recovery of tagatose from solutions of tagatose mixed with other sugars.

DESCRIPTION OF PREFERRED EMBODIMENTS

The Reactants

The choice of initial reactants will depend on which enantiomer of tagatose is desired, on the availability of raw materials, and, to some extent, on what kind of processing equipment is available. This description will focus primarily on the preparation of D-tagatose from D-galactose obtained from lactose. However, any other source of D-galactose, whether pure or in admixture with other compounds could also serve as the raw material. Whey, a by-product from cheese manufacture, or deproteinized whey, whey from which most of the protein has been removed, may be used as raw materials. Also, it should be understood that the techniques described herein are applicable to the preparation of L-tagatose from L-galactose, or from a mixture containing L-galactose. Since L-galactose is not plentiful in nature, it is usually prepared synthetically. Nevertheless, the synthesis described herein is a significant improvement over existing methods for the preparation of L-tagatose.

D-Galactose

The economical production of D-tagatose by this method requires a ready source of D-galactose. The best source of D-galactose is lactose, a plentiful, inexpensive disaccharide which is a by-product from cheese manufacture. Upon acid or enzyme catalyzed hydrolysis, lactose yields and equimolar mixture of the monosaccharides D-glucose and D-galactose. The particular hydrolysis procedure is not critical to the outcome of the process; so any of the known methods are suitable.

With the D-galactose and D-glucose mixture in hand, two process options are possible. The first option is to separate fully or partially the two sugars by chromatography, crystallization, or some other process. When this is done, the D-glucose can be sold or processed further into a salable product such as high fructose corn syrup (HFCS). Lower overall production costs may result from recovering the D-glucose value. Also, this option minimizes waste treatment costs. The second option may be preferred if a means for D-glucose recovery is unavailable. In this case the mixture of sugars is used directly in the isomerization step. The D-glucose (and its isomerization by-products) will be separated from the metal hydroxide-D-tagatose complex after the isomerization step.

Metal Hydroxide

In the isomerization step of this process, the D-galactose is allowed to react under basic conditions with a metal hydroxide to form a stable D-tagatose complex. The most preferable metal hydroxide for low-cost tagatose production is calcium hydroxide ($Ca(OH)_2$) or a mixture of sodium and calcium hydroxides. Normally, the calcium hydroxide will be added to the D-galactose solution as an aqueous slurry. The slurry may be obtained either by mixing $Ca(OH)_2$ with water, or by mixing lime (CaO) with water and allowing the hydration reaction (slaking) to occur. Other metal hydroxides such as barium hydroxide, lead (II) hydroxide, strontium hydroxide, magnesium hydroxide, tin (II) hydroxide, and aluminum hydroxide are also useful.

Catalyst

Certain compounds, added in small amounts, have been found to be beneficial to the isomerization reaction. The most effective compounds are inorganic salts which are soluble in the alkaline reaction medium. Sodium chloride, calcium chloride, magnesium chloride, sodium acetate, potassium chloride, potassium bromide, potassium acetate, calcium bromide, and calcium acetate have all been found to be active catalysts. The requisite amount of catalytic salt is about 1-5 mol % based on the amount of D-galactose. One beneficial effect of the catalyst is an increase in the isomerization rate. Also, when the catalyst is present, it promotes precipitation of the intermediate as a finely divided solid. When no catalyst is added, a thick gel forms which is difficult to filter.

Neutralizing Acid

The neutralization step is conducted using conventional techniques and any acid. It is particularly convenient to use an acid which forms an insoluble salt that can be separated from the tagatose solution by filtration. The remaining ions are then eliminated by passing the solution through standard ion exchange resins. The preferred acid for industrial use, because of its low cost and other process benefits, is carbon dioxide. Neutralizing the intermediate calcium hydroxide-tagatose complex with $CO_2$ results in the formation of the insoluble $CaCO_3$ while the tagatose becomes soluble. The recovered $CaCO_3$ can be reused after converting it with heat back to CaO. Common protic acids such as sulfuric, hydrochloric, and phosphoric acids may also be used to neutralize the intermediate complex.

The Reaction

The process of this invention involves two steps. In the first step, isomerization, D-galactose is allowed to react with calcium hydroxide in aqueous solution, in the presence of a catalyst, and at a relatively low temperature, to form an insoluble calcium hydroxide-D-tagatose complex which is stable under alkaline conditions.

Formation of the insoluble $Ca(OH)_2$-tagatose complex is an important aspect of this reaction for several reasons. First, formation of the insoluble complex strongly drives the equilibrium toward D-tagatose. Secondly, sugars are notoriously unstable under alkaline conditions and are prone to undergo a variety of other isomerization (e.g. formation of D-sorbose) and degradative reactions. The complexation stabilizes the D-tagatose towards these undesirable side reactions. Another advantage is that the insoluble complex can be filtered from the reaction solution to separate it from by-products or other sugars which may have been present in the starting material. This feature greatly aids the economics of the process because pure galactose is not required as the raw material. Instead, a mixture containing galactose, such as that obtained from the hydrolysis of lactose, can be used.

The importance of maintaining a relatively low temperature during the isomerization step was an unexpected and important aspect of this invention. In particular, the temperature should be about $-15°$ to $40°$ C. Higher temperatures result in degrading side-reactions which prevent formation of the desired metal hydroxide-tagatose complex.

In the second step, neutralization, the intermediate is neutralized to yield soluble D-tagatose and a calcium salt.

Isomerization Step

The following is a description of the preferred embodiment of the isomerization step of this process. Variations may be made within the intended scope of the invention, and several of these are described below. It will be apparent that variation in process conditions and requirements will be based in part on the particular reactants and processing equipment which is used.

A reactor vessel, equipped with a strong agitator, and a means for maintaining the reactor contents at a temperature of from about $15°$ to $30°$ C. is charged with a 20% by weight aqueous solution of D-galactose. In a separate vessel an aqueous slurry of $Ca(OH)_2$ is prepared by adding $Ca(OH)_2$ to water, or by adding lime (CaO) to water and allowing the hydration reaction (slaking) to occur. The catalyst, calcium chloride, is added either to the slurry or to the sugar solution. To prevent undesirable side reactions caused by excess heat, the slurry is cooled to $25°$ C. before it is added to the galactose. While stirring the reactor contents, the $Ca(OH)_2$ slurry is added, and most of the $Ca(OH)_2$ dissolves. Stirring is continued, and the reactant contents are maintained at a temperature of about $25°$ C. After about 0.5 to 1 hour a marked increase in the viscosity of the reaction medium occurs. This is a sign that the intermediate calcium hydroxide-tagatose complex is forming. Meanwhile, HPLC analysis is used to monitor the disappearance of galactose, and when conversion exceeds about 80%, the isomerization step is complete. At this point, the reactor contains the intermediate calcium hydroxide-tagatose complex which, after filtration, is a fine, white, sticky solid.

Figure 1:
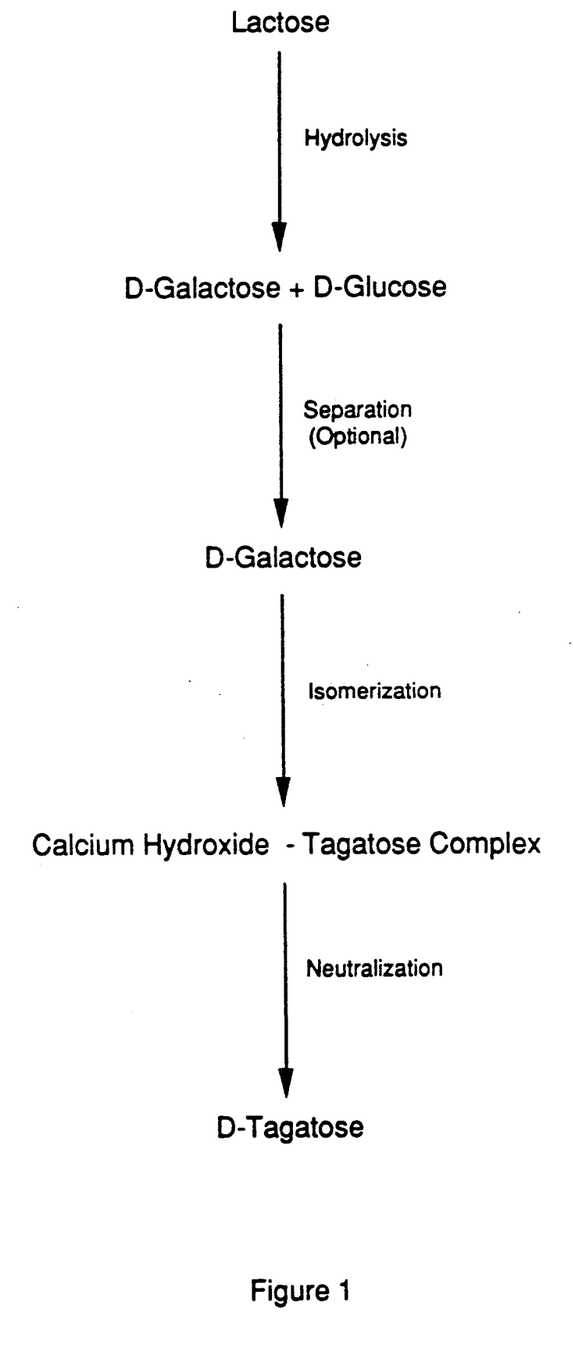
FIG. 1 is a flow chart for the hydrolysis of lactose and subsequent isomerization of D-galactose to D-tagatose.

In alternative embodiments, such as when the raw material is a mixture of lactose, D-glucose, and D-galactose, the preferred procedure will be somewhat different. The following description illustrates the isomerization step starting from lactose without D-galactose separation. FIG. 1 is a flow chart of this process.

The reaction vessel, now equipped with a means for heating the contents, is charged with an aqueous solution containing about 20% by weight lactose, the mixture is heated to 50° C., then lactase enzyme is added. After the hydrolysis proceeds for about 4 hours, HPLC analysis indicates that the solution contains 45% D-glucose, 45% D-galactose, and 10% lactose, based on the total amount of sugars present. The solution is cooled to 25° C. in preparation for the isomerization reaction. The $Ca(OH)_2$ slurry, prepared as before, is added to the sugar mixture, and it is stirred. After about 2 hours the solution has thickened, and a very fine precipitate is present. The precipitate is separated from the mixture by filtration or centrifugation and is washed with a small amount of water. The sticky filter cake is resuspended in water and is now ready for the neutralization step.

Analysis of the Calcium Hydroxide-Tagatose Complex

Figure 4:
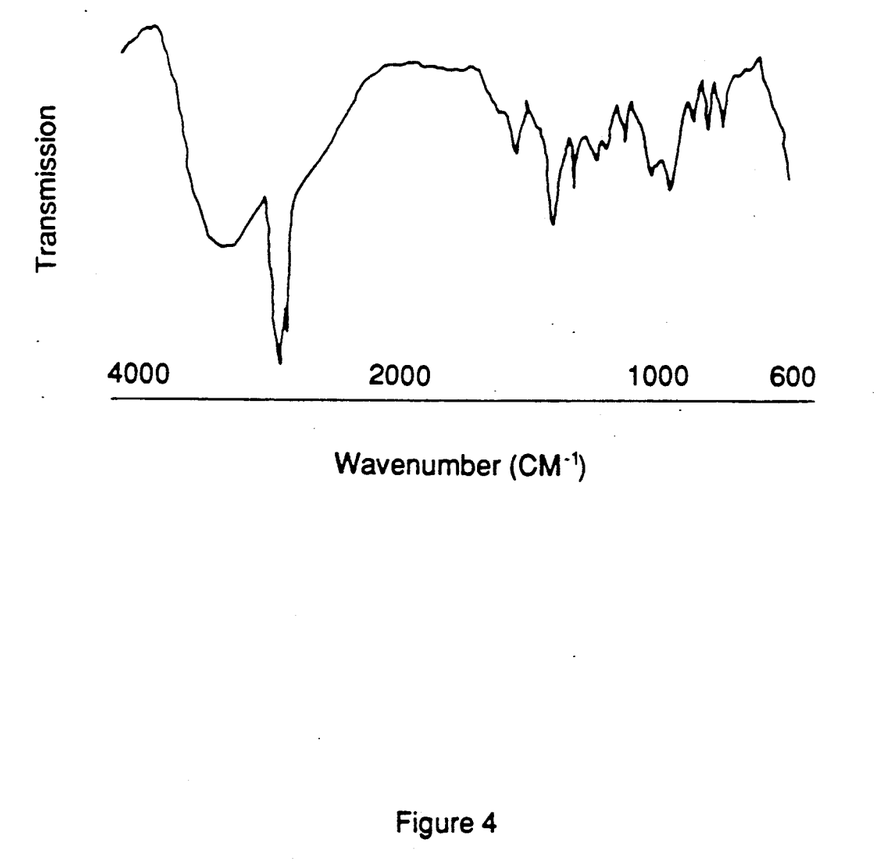
FIG. 4 is an infrared spectrum of the calcium hydroxide-tagatose complex.

After filtration from the reaction mixture and air-drying, the calcium hydroxide-tagatose complex is a white powder. Analysis by HPLC shows that it is 65% by weight tagatose. Elemental analysis indicates that it contains 14.8% by weight calcium. The compound is a hydrated complex of calcium hydroxide and tagatose with the formula $Ca(OH)_2 \cdot tagatose \cdot H_2O$. It has the formula $C_6H_{16}O_9Ca$ and molecular weight 272. The calculated % by weight was, tagatose, 66.2; calcium 14.7. The observed % by weight was, tagatose, 65.8; calcium 14.8. Under vacuum the complex loses water and turns yellow. FIG. 4 shows the infrared spectrum of the anhydrous complex. The anhydrous complex does not have a well defined melting point. It decomposes gradually when heated.

Neutralization Step

The second step of the process of this invention involves neutralization of the intermediate calcium hydroxide-tagatose complex to form a product comprising D-tagatose in solution. Most common inorganic acids such as $H_2SO_4$, HCl, or $H_3PO_4$ and especially $CO_2$ will be suitable for the neutralization step. To carry out the neutralization, about one equivalent of acid is added in relation to the amount of calcium hydroxide-tagatose complex intermediate which is present. It is convenient to monitor the neutralization by following the change in pH. When the pH is below 7, the neutralization is complete. During the addition of acid, the temperature should be kept at 25° C. or below to avoid detrimental side reactions. Once the pH is below 7, the reactor contents will consist of free tagatose and a neutral salt. To recover the purified D-tagatose product, it is necessary to remove the salts, usually by a combination of filtration and ion exchange. After deionization, the solution is ready to be concentrated under vacuum and crystallized. Alternatively, the recovered tagatose may be used directly after neutralization without deionization as a syrup or in further reactions.

Recovery of Pure Tagatose From Crude Tagatose Syrups

Figure 2:
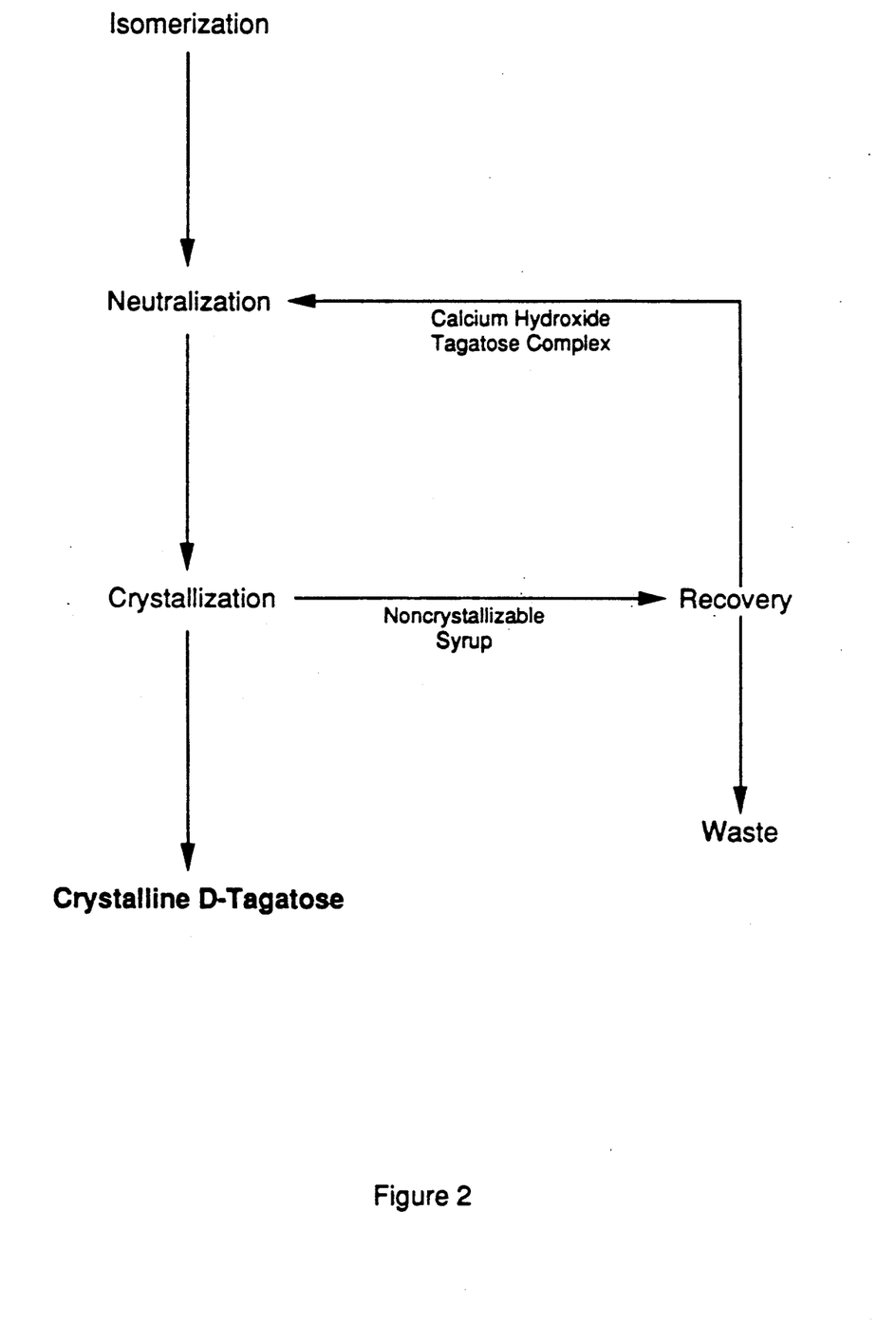
FIG. 2 is a flow chart for the recovery of tagatose from solutions of tagatose mixed with other sugars.

Another embodiment of this invention is for recovering tagatose from crude, noncrystallizable syrups. The final step of a D-tagatose manufacturing process will normally be to crystallize pure D-tagatose from the mother liquor. Some residual tagatose, plus increased proportions of impurities will be left in the filtrate. After several crops of crystals are harvested, the impurity level will build to the point where tagatose will no longer crystallize. The tagatose in crude syrups can be recovered by treatment with calcium hydroxide to form the insoluble calcium hydroxide-tagatose complex, filtration, and neutralization of the complex. FIG. 2 and Example 7 illustrate how the process is useful for recovering tagatose from noncrystallizable syrups in a continuous manufacturing process.

EXAMPLE 1

Isomerization of D-Galactose in the Absence of Catalyst

A $Ca(OH)_2$ slurry was prepared in a small bucket by carefully mixing 4.66 kg CaO with 14 l water in an exothermic reaction. A 230 l capacity stainless steel kettle, equipped with a strong agitator, was charged with 15.0 kg D-galactose and 135 l deionized water and stirred until the sugar dissolved. With the solution stirring at 20° C., the $Ca(OH)_2$ slurry weighing 18.7 kg was gradually added to the kettle. Addition was complete in 1 hour. The progress of the reaction was monitored by HPLC analysis each 0.5 hour, as described below. After 2 hours the mixture had turned to a thick gel; vigorous stirring was continued. After approximately 4 hours, galactose conversion reached greater than 85% and the reaction was stopped by slowly adding 50% by weight phosphoric acid until the pH was 5.8. In this process, the gel dissolved and calcium phosphate precipitated. The calcium phosphate solids were separated from the reaction mixture by centrifugation. The hydrated calcium salts were then rewashed by stirring them with 25 l water in the kettle for an additional hour. Using the centrifuge, the washings were separated and combined with the reaction mixture. The reaction mixture of 150 l was deionized by passing it through columns of AMBERLITE IR-120 (H+ form, 7 l) and then AMBERLITE IRA-68 (free base form, 9 l). AMBERLITE IR-120 is a trademark for a cationic ion exchange resin solid by Rohm and Haas, Philadelphia, Pa. AMBERLITE IRA-68 is a trademark for an anionic ion exchange resin sold by Rohm and Haas, Philadelphia, Pa. The contact time for each resin was at least 20 minutes. The colorless 200 l of eluant was analyzed by HPLC, which showed that the dissolved solids contained 72% D-tagatose based on the amount of D-galactose charged. Because of the large volume of solution, the solution was split into several portions for crystallization. Concentration in vacuo of the first portion of deionized solution gave a thick syrup of 5862 g to which 5871 g of 95% EtOH was added. The stirred mixture was heated to dissolve the syrup, then it was cooled and seeded with a few D-tagatose crystals. After stirring 24 hours, crystalline D-tagatose weighing 2390 g. 93% pure by HPLC, was isolated by vacuum filtration. Recrystallization from 95% EtOH gave 1386 g D-tagatose which had a melting point of 127°-130° C. and the following composition of HPLC: D-tagatose, 97.5%; D-sorbose, 1.00%; unknown No. 1, 0.65%; and unknown No. 2, 1.00% (estimate, unknown No. 2 not well resolved). The remaining portions of deionized solution were concentrated and crystallized in the same way. Two crops of crystals were obtained from each portion. Syrup containing less than 60% D-tagatose would not yield any more crystals.

In total, 4.15 kg of crystalline D-tagatose, mp 131°-133° C. were isolated, a yield of 27.6% based on D-galactose.

Figure 3:
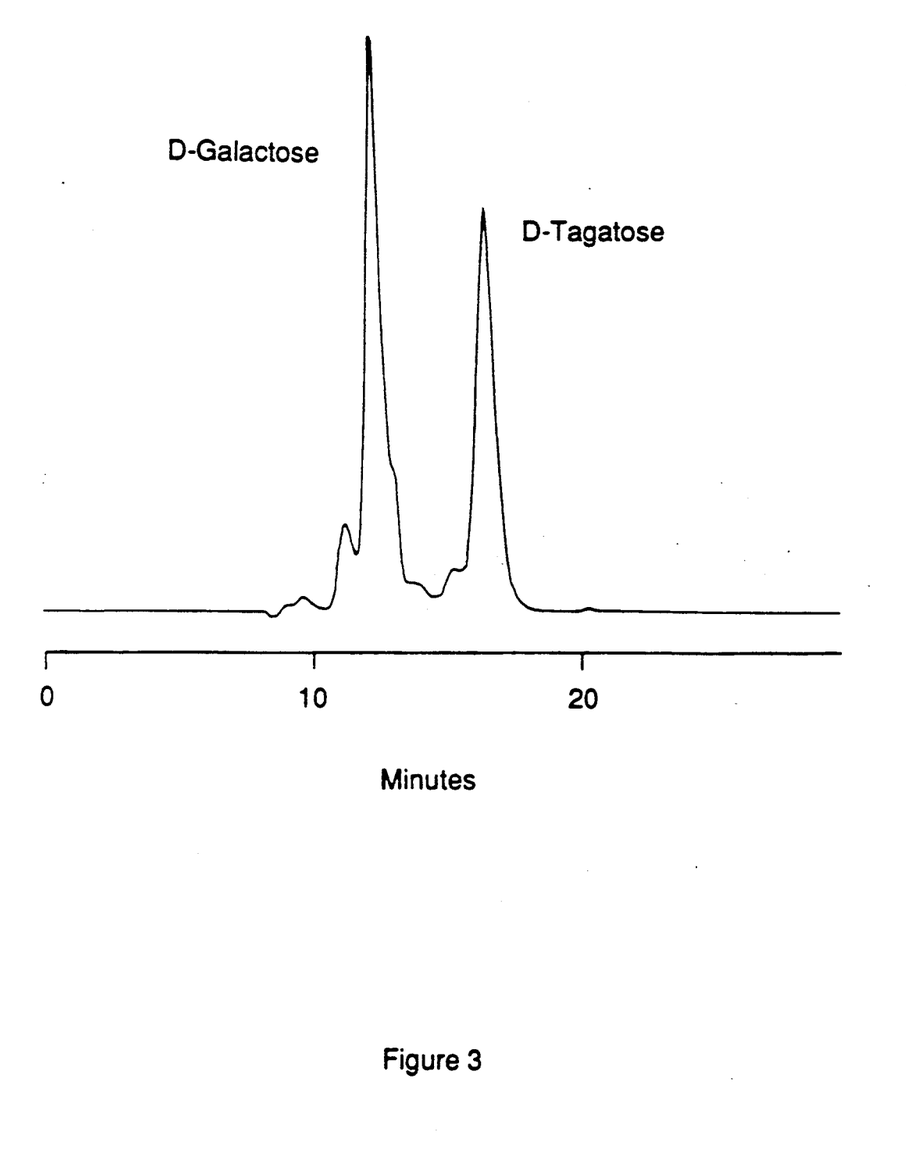
FIG. 3 is a chromatogram showing D-galactose and D-tagatose peaks.

HPLC Monitoring of the Reaction—An aliquot of approximately 1 g of the reaction mixture was withdrawn from the kettle and diluted ten-fold with deionized water. Using a pH probe and a magnetic stirrer, 10% by weight $H_3PO_4$ was added dropwise until the pH was 6.2-6.5. The filtered sample was analyzed using an AMINEX HPX-87C column. AMINEX is a trademark for a carbohydrate analysis HPLC column sold by Bio-Rad, Richmond, Calif. The mobile phase was 50 ppm calcium acetate in deionized, degassed water. The column temperature was 85° C. and the flow rate 0.6 ml per minute. The injection loop was 20 microl and a refractive index detector was used. FIG. 3 is a chromatogram of a sample taken after two hours of reaction showing 45% conversion of D-galactose to D-tagatose. Crystalline D-tagatose samples (25 mg/ml in $H_2O$) were analyzed using the same column and conditions.

EXAMPLE 2

Isomerization of D-Galactose with Catalyst

A $Ca(OH)_2$ and catalyst slurry was prepared by carefully mixing 4.66 Kg CaO and 0.231 kg calcium chloride with 14 l water in an exothermic reaction. The 230 l capacity stainless steel kettle was charged with 15.0 kg D-galactose and 135 l deionized water and the contents were stirred until the sugar dissolved. With the solution stirring at 20° C., the $Ca(OH)_2$ and calcium chloride slurry of 18.7 kg was gradually added to the kettle. After addition was complete, the pH of the solution was measured. A small amount of 10% NaOH solution was added to increase the pH to 12.5. The progress of the reaction was monitored as in Example 1 by HPLC analysis each 0.5 hour. After 0.5 hour the mixture had turned to a thick gel, and a precipitate began to form. After approximately 1.5 hours, when galactose conversion had reached greater than 85%, the reaction was stopped by bubbling carbon dioxide into it until the pH had dropped to 6.5. In this process the precipitate dissolved and a precipitate of calcium carbonate formed. The calcium carbonate was separated from the reaction mixture which contained the sugar solution by centrifugation. The reaction mixture which had a volume of 150 l was deionized as in Example 1. The 200 l of colorless eluant, when analyzed by HPLC, as in Example 1, showed the presence of 10.8 kg D-tagatose, a yield of 72% based on D-galactose charged.

EXAMPLE 3

Tagatose Synthesized From Lactose

The 230 l capacity stainless steel kettle was charged with 10.0 kg lactose and 40 l deionized water, stirred, and heated to 50° C. TAKAMINE Brand Fungal Lactase 30,000 enzyme was added to the mixture, which was stirred. TAKAMINE Brand Fungal Lactase 30,000 is a trademark for lactase enzyme isolated from *Aspergillus oryzae* and sold by Miles Laboratories, Inc., Elkhart, Ind. After 6 hours HPLC analysis indicated that lactose hydrolysis was essentially complete. The mixture contained approximately 10% lactose, 45% D-glucose, and 45% D-galactose. The reaction mixture was cooled to 25° C. in preparation for the isomerization step. With cooling, 154 g calcium chloride was dissolved in the hydrolyzed lactose solution, then the $Ca(OH)_2$ slurry, prepared by mixing 2.0 kg $Ca(OH)_2$ with 2.5 l water, was gradually added to the kettle. After addition was complete, the pH of the solution was measured. A small amount of 10% NaOH solution was added to increase the pH to 12.5. After 3.0 hours the mixture had thickened and a precipitate had formed. The precipitate was filtered from the reaction mixture using a centrifuge to give a pasty filter cake. The filter cake was resuspended in the kettle with 25 l of water, and the slurry was neutralized by $CO_2$ addition. The final pH was 6.5. In the neutralization process, the filter cake dissolved and a precipitate of calcium carbonate was formed. The calcium carbonate was separated from the reaction mixture by centrifugation. The 35 l of reaction mixture was deionized as in Example 1. The 50 l of colorless eluant was assayed by HPLC as in Example 1 and found to contain 2.38 kg of D-tagatose, a yield of 47.6%.

EXAMPLE 4

Tagatose Synthesized from Lactose, Glucose Recovered

A 100 ml flask containing 10.0 g lactose and 50 ml water was warmed to 50° C. and treated with 80 mg lactase 30,000 enzyme as in Example 3. After 6 hours the solution was analyzed by HPLC and found to contain 10% lactose, 45% D-glucose, and 45% D-galactose, based on the lactose added. The mixture was heated to 75° C. briefly to denature the protein, and was then filtered. A 2.5 cm interior diameter by 60 cm length glass column was packed with about 300 ml of BIO-RAD AG 50W-X8 resin in the calcium form, minus 400 mesh. BIO-RAD AG 50W-X8 is the trademark for a cationic ion exchange resin sold by Bio-Rad, Richmond, Calif. The column was heated to 70° C. The mobile phase was deionized water which had been filtered and degassed and which was pumped at a flow rate of 4.0 ml per minute. Typical pressure was 30 psig. The sample injection loop was 10 ml. The run time was approx. 55 minutes. The filtered reaction mixture described above was concentrated to 30% by weight solids, then injected in portions into the column. By using a refractive index detector to monitor the eluant, the mixture was separated into two groups of fractions. The combined first group of fractions contained 0.8 g of lactose and 4.2 g D-glucose. The combined second group of fractions contained 0.3 g of D-glucose and 4.4 g of D-galactose. The second group of fractions was concentrated to 10% by weight solids for the isomerization step. The D-galactose solution, stirred at room temperature in a small flask, was treated with 2.0 g calcium hydroxide and 0.15 g calcium chloride, and the precipitate formed within 1.5 hours. The precipitate of calcium hydroxide-tagatose complex was neutralized with $CO_2$ to give 2.2 g D-tagatose.

EXAMPLE 5

Isomerization of D-Galactose with Barium Hydroxide

A 100 ml Erlenmeyer flask is charged with 150 ml water, 15.0 g D-galactose, 25.2 g Ba(OH)$_2$ octahydrate, and 0.83 g BaCl$_2$. The mixture is stirred at room temperature while the isomerization is monitored by HPLC as in Example 1. After 3 hours, analysis showed 80% conversion of D-galactose to D-tagatose and the reaction is stopped by bubbling CO$_2$ into the mixture. The neutralized mixture is filtered to remove BaCO$_3$, deionized, concentrated in vacuo, and crystallized to give D-tagatose.

EXAMPLE 6

Isomerization of L-Galactose, Calcium Acetate Catalyst

To a 25 ml Erlenmeyer flask, equipped with a magnetic stirrer, was added 0.5 g L-galactose, 5 ml water, 0.2 g calcium hydroxide, and 22 mg calcium acetate. The mixture was stirred. After 2 hours, the solution was filtered to collect the calcium hydroxide-L-tagatose complex that had formed. The sticky complex was resuspended in 5 mL of H$_2$O, and CO$_2$ was bubbled through the slurry until the pH was below 7. The solution, after filtering off the calcium carbonate, was deionized as in Example 1 and concentrated in vacuo to a syrup which, after seeding with a few L-tagatose crystals, provided 0.22 of pure L-tagatose, a 44% yield.

EXAMPLE 7

Recovery of Pure Tagatose from a Crude Syrup

A 22 l flask equipped with a strong mechanical stirrer was charged with 9.5 l of a sugar mixture containing 20% by weight solids which consisted of 53% D-tagatose, 21% D-galactose, 16% D-sorbose, 5% glucose, 2% mannose, and 3% fructose. To the mixture 414 g Ca(OH)$_2$ and 15.0 g CaCl$_2$ were added and the mixture was stirred at room temperature. After 2 hours, the calcium hydroxide-D-tagatose complex precipitate was collected on a large Buchner funnel and washed with a little water. The precipitate was neutralized with CO$_2$ to afford 420 g of pure D-tagatose.

Since the above disclosure is subject to variations, it should be understood that the above examples are merely illustrative and that the invention disclosed herein should be limited only by the claims.

We claim:

1. A process for the synthesis of tagatose from galactose comprising the steps of:
   A. isomerizing an aqueous solution of galactose with a metal hydroxide in the presence of catalytic amounts of a soluble alkaline metal salt or alkaline earth salt, at a pH greater than about 10, and at a temperature of about $-15°$ to $40°$ C., until an insoluble precipitate consisting substantially of a metal hydroxide-tagatose complex is formed,
   B. neutralizing said precipitate with a suitable acid until the pH is below about 7, and
   C. recovering the tagatose.

2. The metal hydroxide-tagatose complex formed in claim 1.

3. The metal hydroxide-tagatose complex with the formula Ca(OH)$_2$·tagatose.

* * * * *

UNITED STATES PATENT AND TRADEMARK OFFICE
CERTIFICATE OF CORRECTION

| | |
|---|---|
| PATENT NO. | : 5,078,796 |
| APPLICATION NO. | : 07/667591 |
| DATED | : January 7, 1992 |
| INVENTOR(S) | : Beadle et al. |

It is certified that error appears in the above-identified patent and that said Letters Patent is hereby corrected as shown below:

On the title page,
[*] delete "The portion of the term of this patent subsequent to Mar. 26, 2008 has been disclaimed." and insert --This patent is subject to a terminal disclaimer.--.

Signed and Sealed this

Fifth Day of February, 2008

JON W. DUDAS
*Director of the United States Patent and Trademark Office*